United States Patent
Kemp et al.

(10) Patent No.: US 9,347,765 B2
(45) Date of Patent: May 24, 2016

(54) REAL TIME SD-OCT WITH DISTRIBUTED ACQUISITION AND PROCESSING

(75) Inventors: Nathaniel J. Kemp, Austin, TX (US); Austin Broderick McElroy, Austin, TX (US); Joseph P. Piercy, Helotes, TX (US)

(73) Assignee: Volcano Corporation, San Diego, CA (US)

( * ) Notice: Subject to any disclaimer, the term of this patent is extended or adjusted under 35 U.S.C. 154(b) by 1116 days.

(21) Appl. No.: 11/868,334

(22) Filed: Oct. 5, 2007

(65) Prior Publication Data

US 2009/0093980 A1 Apr. 9, 2009

(51) Int. Cl.
| | |
|---|---|
| G01B 9/02 | (2006.01) |
| G01N 21/47 | (2006.01) |
| A61B 5/00 | (2006.01) |
| G06T 11/00 | (2006.01) |
| G06T 1/20 | (2006.01) |
| A61B 19/00 | (2006.01) |

(52) U.S. Cl.
CPC .......... *G01B 9/02089* (2013.01); *A61B 5/0066* (2013.01); *G01B 9/02084* (2013.01); *G01B 9/02091* (2013.01); *G01N 21/4795* (2013.01); *G06T 1/20* (2013.01); *G06T 11/003* (2013.01); *A61B 2019/5276* (2013.01); *G06T 2207/10101* (2013.01); *G06T 2207/10132* (2013.01); *G06T 2207/20056* (2013.01); *G06T 2211/428* (2013.01)

(58) Field of Classification Search
USPC ......... 382/100, 128, 131, 254, 260, 266–269; 702/77; 600/425, 476; 709/201–203, 709/223
See application file for complete search history.

(56) References Cited

U.S. PATENT DOCUMENTS

| | | | |
|---|---|---|---|
| 6,091,496 A | 7/2000 | Hill | 356/351 |
| 6,480,285 B1 | 11/2002 | Hill | 356/492 |
| 6,847,449 B2 | 1/2005 | Bashkansky | 356/364 |
| 7,010,458 B2 | 3/2006 | Wilt | 702/180 |
| 7,249,357 B2 | 7/2007 | Landman et al. | 718/102 |
| 2002/0186818 A1 | 12/2002 | Arnaud et al. | 378/165 |
| 2003/0069723 A1* | 4/2003 | Hegde | 703/15 |
| 2003/0103212 A1* | 6/2003 | Westphal et al. | 356/479 |
| 2003/0212491 A1 | 11/2003 | Mitchell et al. | 702/1 |
| 2004/0186369 A1 | 9/2004 | Lam | 600/407 |
| 2005/0036150 A1* | 2/2005 | Izatt et al. | 356/479 |
| 2005/0122333 A1* | 6/2005 | Sumanaweera et al. | 345/502 |
| 2005/0243322 A1 | 11/2005 | Lasker et al. | 356/432 |
| 2005/0251567 A1 | 11/2005 | Ballew et al. | 709/223 |
| 2006/0132790 A1 | 6/2006 | Gutin | 356/479 |
| 2006/0179255 A1 | 8/2006 | Yamazaki | 711/147 |
| 2006/0204119 A1 | 9/2006 | Feng et al. | 382/250 |

(Continued)

FOREIGN PATENT DOCUMENTS

WO  WO 2007-058895  5/2007 ............ G03B 17/00

OTHER PUBLICATIONS

International Search Report, pp. 1-3 (Jan. 16, 2009).

(Continued)

*Primary Examiner* — Kim Vu
*Assistant Examiner* — Nathan Bloom
(74) *Attorney, Agent, or Firm* — Brown Rudnick LLP; Thomas C. Meyers

(57) ABSTRACT

The present invention relates to distributed computing system to acquire, process, and display OCT images at real-time frame rates.

16 Claims, 10 Drawing Sheets

(56) References Cited

U.S. PATENT DOCUMENTS

| | | | |
|---|---|---|---|
| 2006/0293597 A1 | 12/2006 | Johnson et al. | 600/437 |
| 2007/0027390 A1* | 2/2007 | Maschke et al. | 600/425 |
| 2007/0036417 A1 | 2/2007 | Argiro et al. | 382/131 |
| 2007/0038121 A1 | 2/2007 | Feldman et al. | 600/476 |
| 2007/0229801 A1* | 10/2007 | Tearney et al. | 356/73 |
| 2007/0258094 A1* | 11/2007 | Izatt et al. | 356/456 |
| 2007/0263171 A1* | 11/2007 | Ferguson et al. | 351/206 |
| 2008/0013093 A1* | 1/2008 | Izatt et al. | 356/456 |
| 2008/0043024 A1* | 2/2008 | Schiwietz et al. | 345/442 |
| 2008/0181477 A1* | 7/2008 | Izatt et al. | 382/128 |
| 2011/0255095 A1* | 10/2011 | Jiang et al. | 356/479 |

OTHER PUBLICATIONS

Written Opinion, pp. 1-5 (Jan. 16, 2009).

Communication Mechanisms for Distributed Real-Time Applications, NI Developer Zone, http://zone.ni.com/devzone/cda/tut/p/id/3105, accessed Jul. 23, 2007.

"Deterministic Data Streaming in Distributed Data Acquisition Systems, NI Developer Zone, What is Developer Zone?", http://zone.ni.com/devzone/cda/tut/p/id/3105, accessed Jul. 23, 2007.

* cited by examiner

REAL TIME SD-OCT WITH DISTRIBUTED ACQUISITION AND PROCESSING

BACKGROUND OF THE INVENTION

The present invention relates generally to computing systems, and more particularly related to Optical Coherence Tomography ("OCT") systems and methods Spectral-domain optical coherence tomography ("SD-OCT"), also known as Fourier-domain OCT (FD-OCT), does not require modulation of the reference arm length and therefore has potential for faster image acquisition rates. SD-OCT is based on spectral interferometry, where recombined light from reference and sample arms is spectrally separated, detected and converted into a depth profile. Three-dimensional data sets can therefore be rapidly acquired, opening the possibility of comprehensive screening.

OCT generates cross sectional imaging of tissues with micro-scale resolution by measuring the echo time delay of backscattered or backreflected light. Fourier Domain OCT ("FD-OCT") can obtain a high sensitivity and imaging speed by acquiring the optical spectrum of sample light interfered with light from a single stationary reference reflector using an interferometer. Swept-Source OCT ("SS-OCT"), time-encodes the wavenumber by rapidly tuning a narrowband source over a broad optical bandwidth.

High-speed OCT imaging systems generate data at high bit rates, roughly 10 s-100 s Megabytes/sec. Currently, the central processor unit ("CPU") is performing all FFT calculations. The present invention solves the problems of effectively acquiring, processing, and displaying OCT imaging at real time frame rates.

SUMMARY OF THE INVENTION

The present invention relates to distributed computing system to acquire, process, and display OCT images at real-time frame rates.

The foregoing summary, as well as the following detailed description of preferred embodiments of the invention, will be understood when read in conjunction with the appended drawings. For the purpose of illustrating the invention, there is shown in the drawings embodiments which are presently preferred. It should be understood, however, that the invention is not limited to the precise arrangements and configurations shown.

BRIEF DESCRIPTION OF THE DRAWINGS

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PREFERRED EMBODIMENTS

Figure 1:
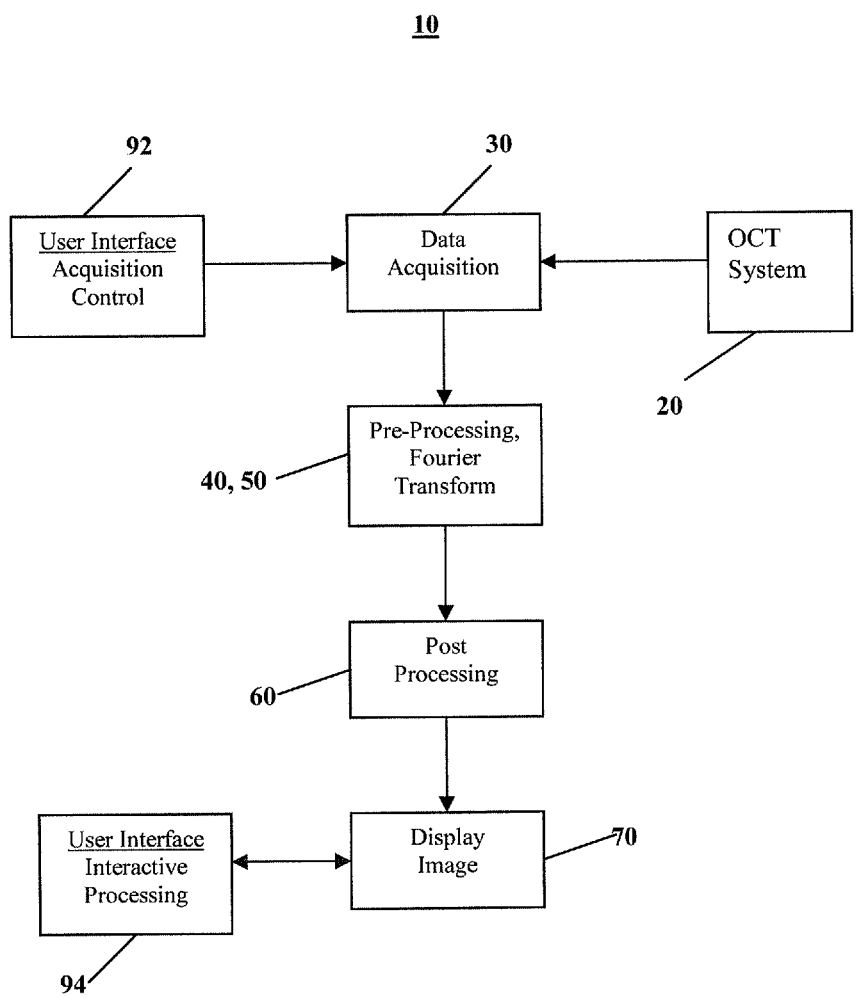
FIG. 1 is the distributed computing system.

In the accompanying figures, like elements are identified by like reference numerals among the several preferred embodiments of the present invention.

Figure 2A:
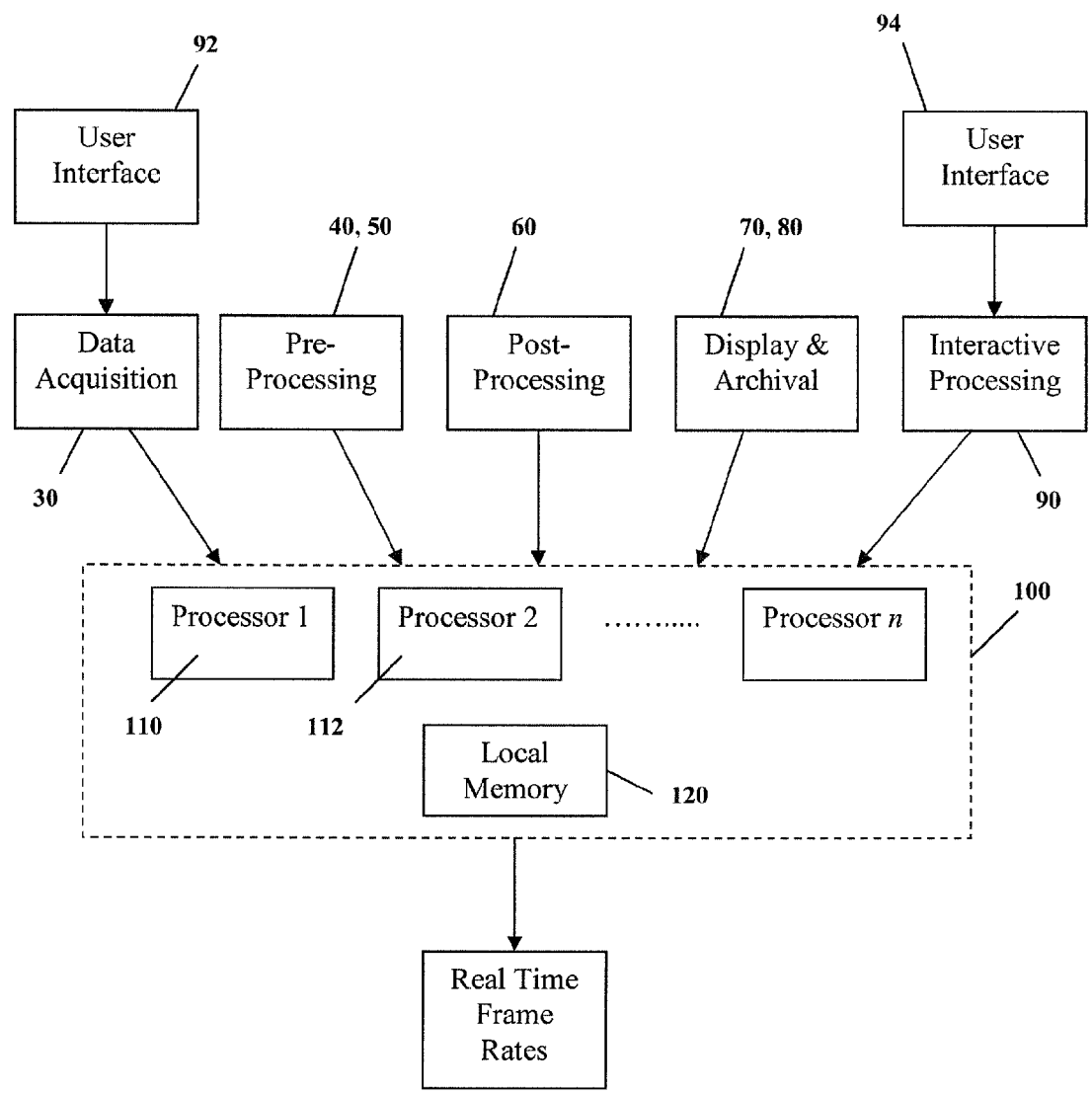
FIGS. 2A and 2B are embodiments of the invention.
Figure 2B:
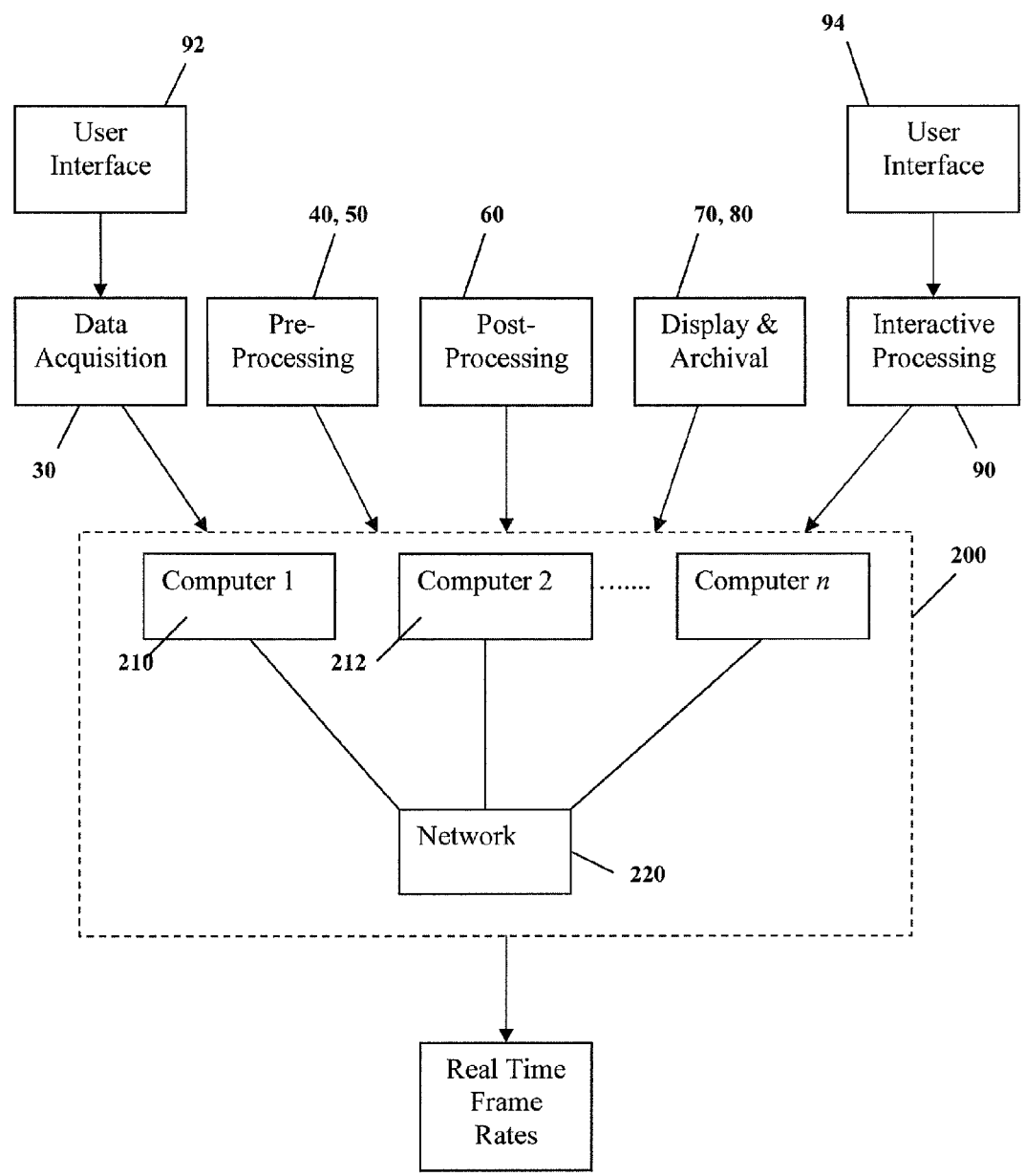

Generally speaking, the invention is a distributed computing system 10 to acquire, process, and display OCT images at real-time frame rates. As shown in FIG. 1, the distributed computing system 10 is coupled to an OCT system 20 with a plurality of OCT steps including a data acquisition step 30, a pre-processing step 40 and a Fourier transformation step 50, an image post-processing step 60, a display step 70, and an archival step 80. The OCT system 20 generates an OCT signal, which is then processed and divided amongst the OCT steps. The distributed computing system 10 accomplishes the plurality of OCT steps using two or more separate but networked computers or processors. The user interacts with the distributed computing system 10 before acquisition with a user interface 90 to either set up imaging parameters and start data acquisition 30. The user also interacts with the distributed computing system 10 after display 70 with a user interface 92 to request additional post-processing, interactive processing, measurement of image features, playback control, etc. The OCT steps can be assigned to a cluster of processors 100 including multiple processors or in any combination depending on the number of processors available and the efficiency of each processor type at performing each operation. In one embodiment of the invention, one processor 110 could be used for the data-acquisition step 30, while a second processor 112 could be used for the pre-processing step 40, the Fourier transformation step 50, the post-processing step 60, the display step 70, and the post-display interaction 80, as shown in FIG. 2A. The processors 110 and 112 can share local memory 120 or include separate memory sources. In another embodiment of the invention, a cluster of computers 200 is implemented for the OCT steps, where a single computer 210 may be used for all the user interaction, a second computer 212 for the acquisition step, the Fourier Transformation step, and the post-processing, as shown in FIG. 2B. Each computer in the cluster 200 is connected by a network 220.

A "computer" can be any electronic instrument with a microprocessor or central processing unit ("CPU") and local memory or Random Access Memory ("RAM") and running an operating system and with some communication capability. The computer can include a traditional personal computer, workstation, network computer node, graphics card with graphics processing unit ("GPU"), dedicated digital signal processor ("DSP") expansion card, etc.

Each computer includes an "operating system", which is software running on the computer and includes, but is not limited to, Windows, Linux, UNIX, Solaris, Mac OS, a real-time operating system, etc. "Communication capability" is any means of communicating OCT data and other commands between computers in the network. OCT data and commands do not necessarily need to be communicated over the same bus/network. Multiple communication networks can be employed. Communication capability includes both communication hardware (e.g. a network card) and software based communication protocol. A non-exhaustive list of standardized digital communication capabilities (hardware and software) includes: 100 GBit Ethernet, 10 GBit Ethernet, GigaBit Ethernet, TCP/IP, UDP, Firewire, USB 2, SCSI, SATA, eSATA, PCI, PCI-Express, fiber optic, IDE, etc. Additionally, a custom software protocol could be written to optimize transfer speed over the listed hardware options, or could employ other non-specific digital I/O cards which are commonly available.

Transmission between computer nodes in the OCT system can be buffered (internally or externally) through memory/storage hardware such as RAM, magnetic hard disk, flash RAM, etc. These buffers can be controlled by the computer nodes or have dedicated controllers which subscribe to the network protocol being used. Examples of these buffers include external RAM disks, network-attached storage (NAS) disks, a storage area network (SAN), etc.

The software, such as computer-executable instructions, manages the workload of attached computers and routes tasks accordingly to maximize overall operation speed. Thus, the program flow shown above can be further broken down into small parts and distributed to multiple computers on the network. The software, such as program modules, also may be executed by one or more computers or other devices. Generally, program modules include computer code, routines, programs, objects, components, data structures, etc. that performs particular tasks or implement particular abstract data types. The image construction software and other operating software are implemented in the distributed computing environments where tasks are performed by remote processing devices that are linked through a communications network. The image construction software can then generate real-time images of the OCT signal.

Figure 3:
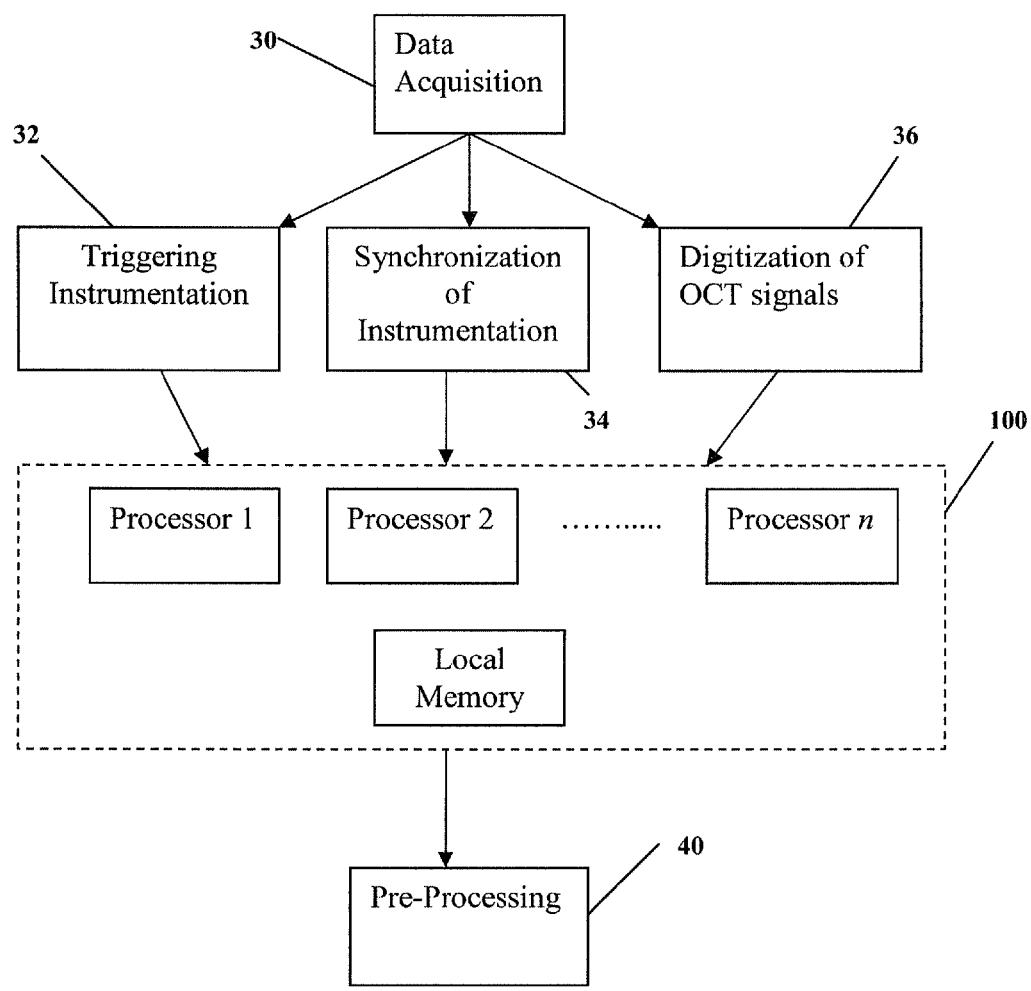
FIG. 3 is a schematic of the data-acquisition steps.

The data acquisition step 30 includes a triggering step 32, a synchronization step 34, and a digitization step 36, as shown in FIG. 3. The triggering step 32 triggers the instrumentation and the synchronization step synchronizes the instrumentation of the OCT system, such as the clocking of the light source. The digitization step 36 digitizes the OCT signals using a high-speed Analog-to-Digital ("A/D") converter (AlazarTech, Montreal, Canada). The A/D converter is typically connected to and controlled by a host computer and communicates with the host processor over a data bus (e.g. Peripheral Component Interconnect "PCI", PCIe, PCI extension for Instrumentation "PXI", PXIe, etc.) The A/D converter may or may not have onboard random access memory ("RAM"), and may or may not immediately transfer some or all of the acquired data to the host computer's RAM. The A/D converter may also be a standalone instrument (e.g. digitizing oscilloscope) with onboard RAM and means of transferring data externally to other instruments or computers through a data bus. Each of the data acquisition steps 30 may be further divided up and assigned to separate computers 100 in the distributed computing system 10. The data acquisition steps 30 are then followed by the pre-processing step 40 and the Fourier Transformation step 50.

Figure 4A:
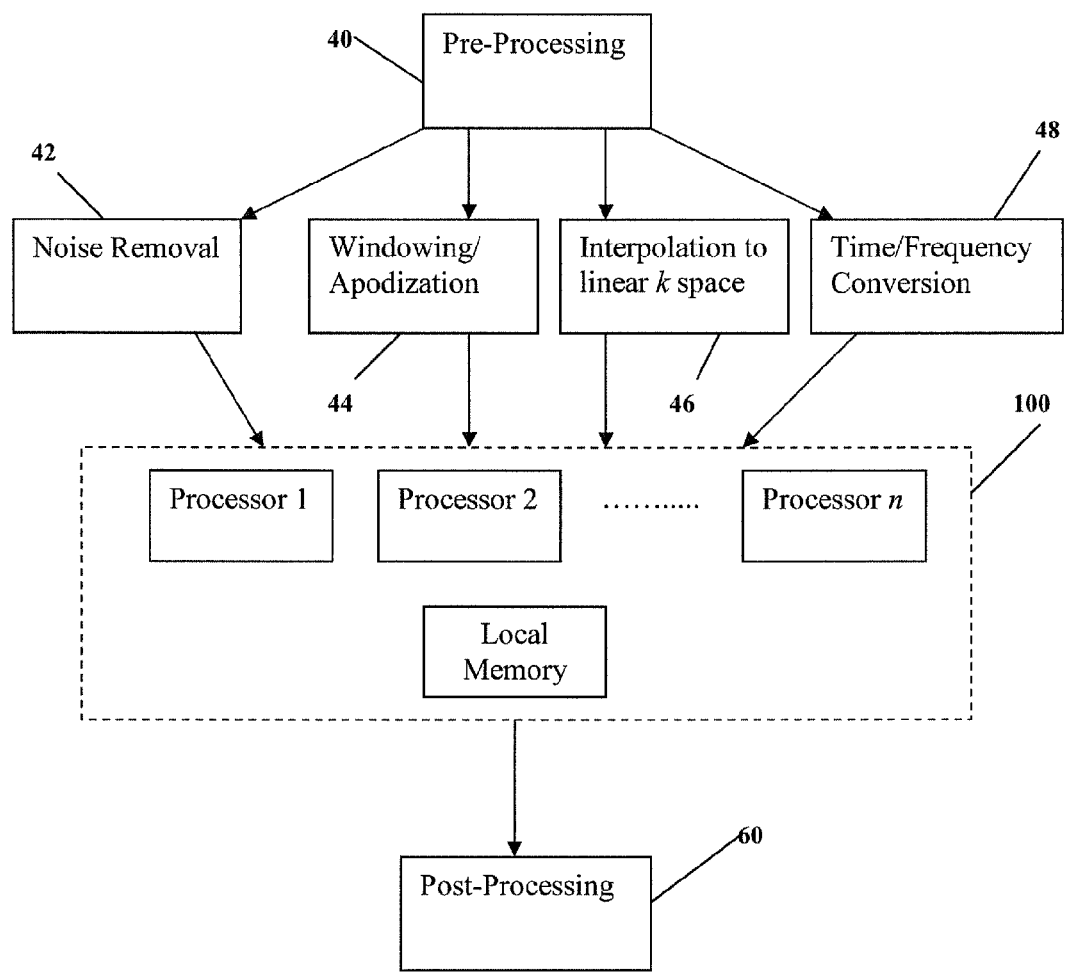
FIG. 4A is a schematic of the pre-processing steps.

As shown in FIG. 4A, the pre-processing step 40 includes pre-processing steps such as noise removal 42, windowing/apodization 44, and interpolation to linear wavenumber space 46, and then time/frequency conversion 48, usually by means of the Fast Fourier Transform ("FFT"), the Fourier transformation step 50, or other frequency transforming operation. Noise removal is necessary for OCT operations, as noise results from the light source, interferometer, and detector and electronics. Windowing/apodization is a mathematical technique used to reduce the Gibbs phenomenon "ringing" which is produced in a spectrum obtained from a truncated interferogram. The pre-processing step 40 is typically a processor intense operation and thus benefits from the distributed computing system 10, and may further be divided and assigned to separate processors or computers 100.

Figure 4B:
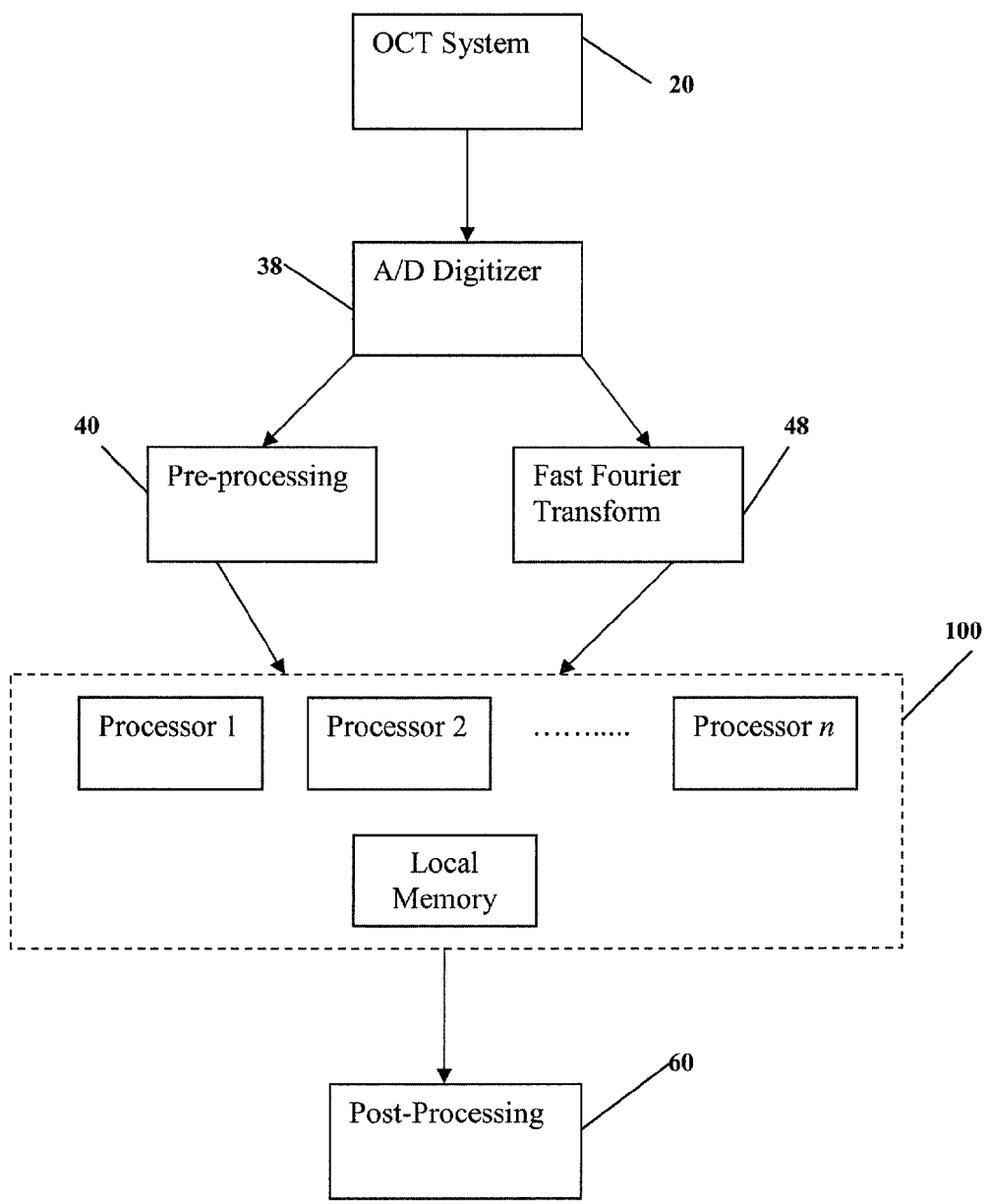
FIG. 4B is a schematic of the digitizer.

In another embodiment of the invention, an on-board A/D digitizer 38 acquires the OCT signal from the OCT system 20 and directly performs the pre-processing steps 40 and Fast Fourier Transforms in the A/D digitizer card 38, as shown in FIG. 4B. The on-board processing is accomplished with a Field Programmable Gate Array ("FPGA"), DSP, microprocessor, etc. Field Programmable Gate Array is a semiconductor device containing programmable logic components called "logic blocks", and programmable interconnects. The software that manages the on-board processing resides in the firmware of the A/D digitizer card. Firmware is a computer program that is embedded in the hardware device of the A/D digitizer card, such as in the microcontroller. The firmware acquires the required number of waveforms on the A/D digitizer's on-board memory using standard Multiple Record mode. The Multiple Record mode allows multiple waveforms to be captured and stacked in the on-board memory of the A/D digitizer 38. The waveform data is downloaded to the host computer through the on-board FFT algorithm. The FFT algorithm is structured in a pipeline fashion, which does not reduce the data-transfer speed. Before the FFT is performed on the A/D digitizer; a time-domain window may be applied to the data. The windowing/apodization functions are provided and arbitrary symmetric windowing functions of any design may be selected. After the pre-processing steps 40 and the FFT 36 on the A/D digitizer 38 have been performed, the post-processing steps 60 and image display step 70 can be performed on a cluster of processors 100.

Figure 5:
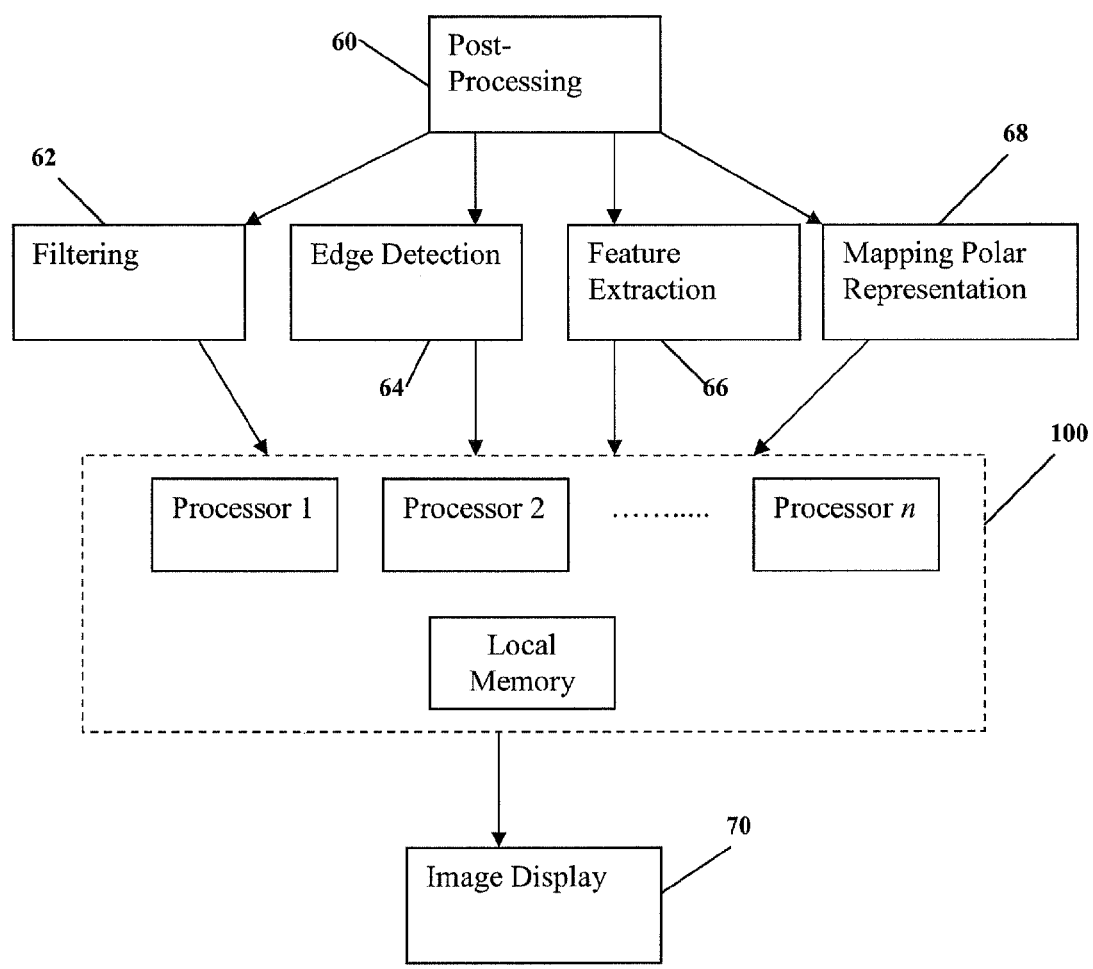
FIG. 5 is a schematic of the post-processing steps.

As shown in FIG. 5, the image post-processing steps 60 can include filtering 62; edge detection 64, feature extraction 66, and mapping polar representations 68. Filtering 62 includes de-noising, speckle removal, etc. by means of any number of well-known image processing algorithms. Filtering may be accomplished by adaptive filtering or low pass filtering by using mean, median, and Gaussian filters. Speckle removal techniques include spatial averaging, frequency compounding, polarization averaging, and image processing techniques. Edge detection 66 and feature extraction 68 are advanced automated processes. Feature extraction 68 includes image segmentation, image measurements, and image display. Edge detection 66 may include a Marr-Hildreth algorithm, for example. The mapping of polar representations is required when images are acquired in a cylindrical or helical scanning pattern are likely to be mapped from rectangular to polar representation. The post-processing steps 60 can be divided and assigned to separate processors or computers 100 in the distributed computing system 10. After the post-processing steps 60, real-time image display 70 follows.

Figure 6:
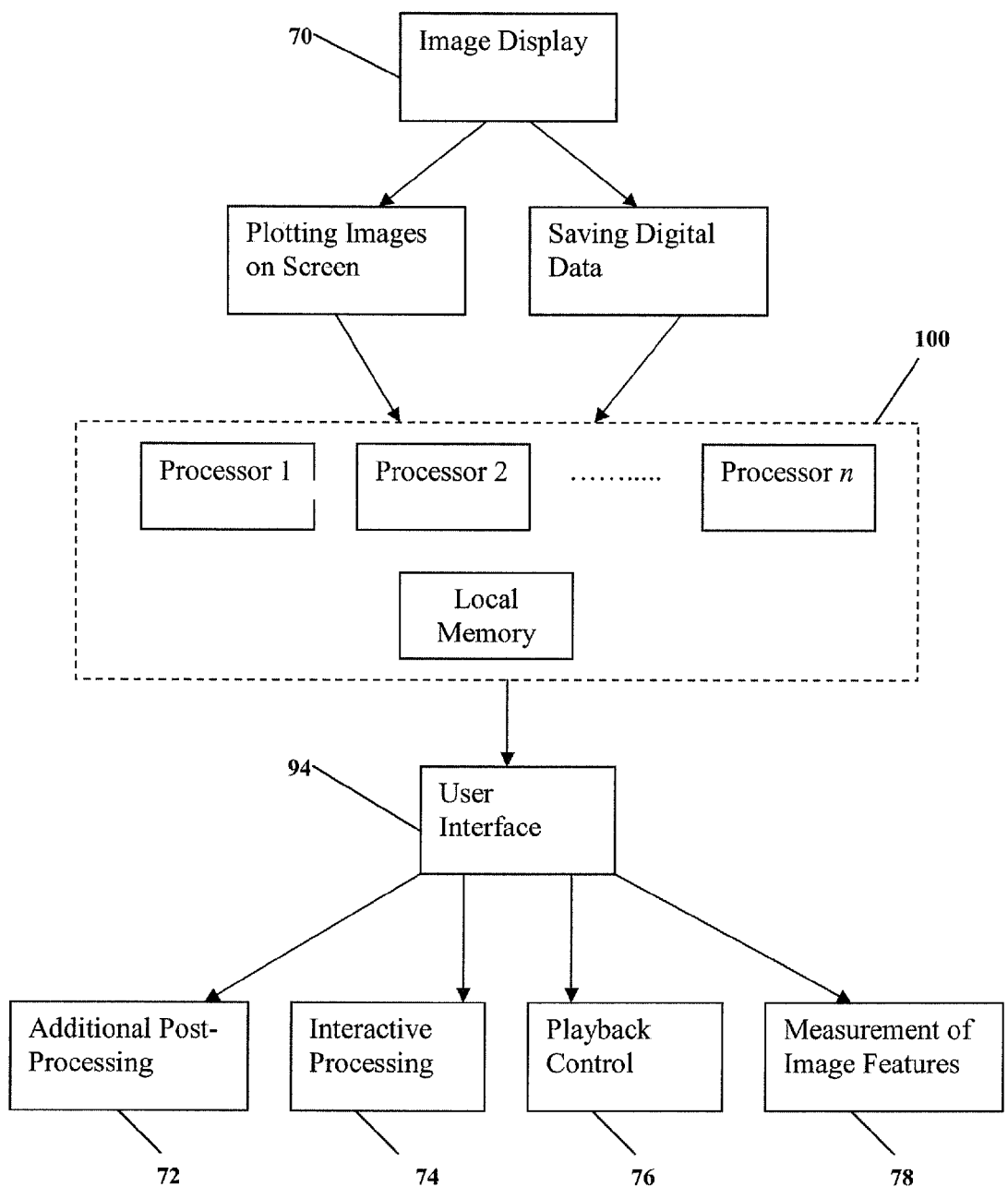
FIG. 6 is a schematic of the image display steps.
Figure 7:
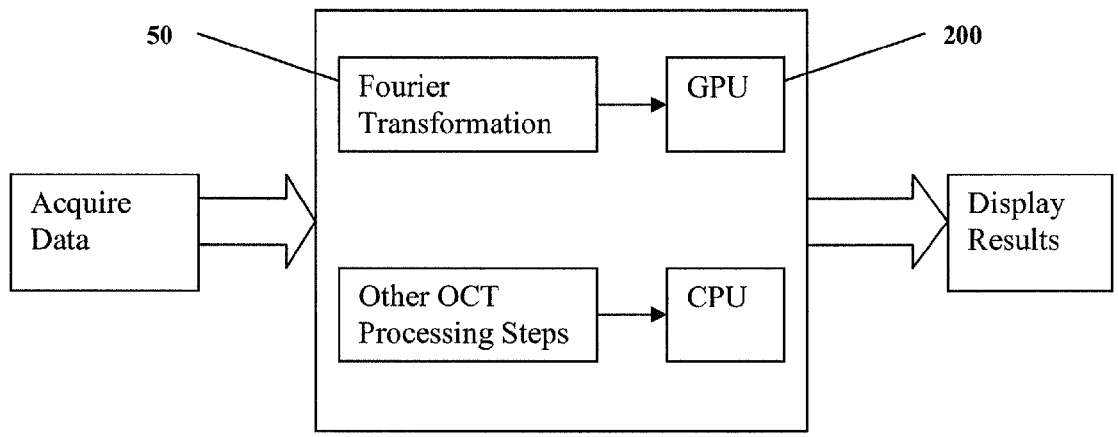
FIG. 7 is one embodiment of the invention.

As shown in FIG. 6, the display 70 and archival 80 of the OCT data simply involves plotting images on a screen for immediate viewing and saving digital data to disk (either directly from the A/D converter and/or the final processed image and/or at any intermediate step. After real-time display, the user can request additional post-processing 72, interactive processing 74, measurement of image features 76, and playback control 78 through user interface 94.

Using the GPU to Perform FFT Function on OCT Data

In another embodiment of the invention, the distributed computing system 10 further includes a Graphics Processing Unit ("GPU") processor 200 to implement the Fourier transformation step 50. By offloading the CPU intensive FFT calculations to the GPU, other OCT steps can be performed by other processors for the distributed computing system 10. Using an NVIDIA programming kit, the FFT transform is implemented on a modern, high speed GPU to reduce the time it takes to calculate the FFT, improving all software aspects of the OCT system 20. There are several different C implementations of this code that exist for various NVIDIA and ATI video cards.

In another embodiment of the invention, PCI cards may include 1-8 DSP which may perform the Fourier transformation step 50 in the distributed computing system 10. Alternatively, the FPGA could perform the Fourier transformation step 50 in the distributed computing system 10.

Ultrasound/OCT System

Figure 8:
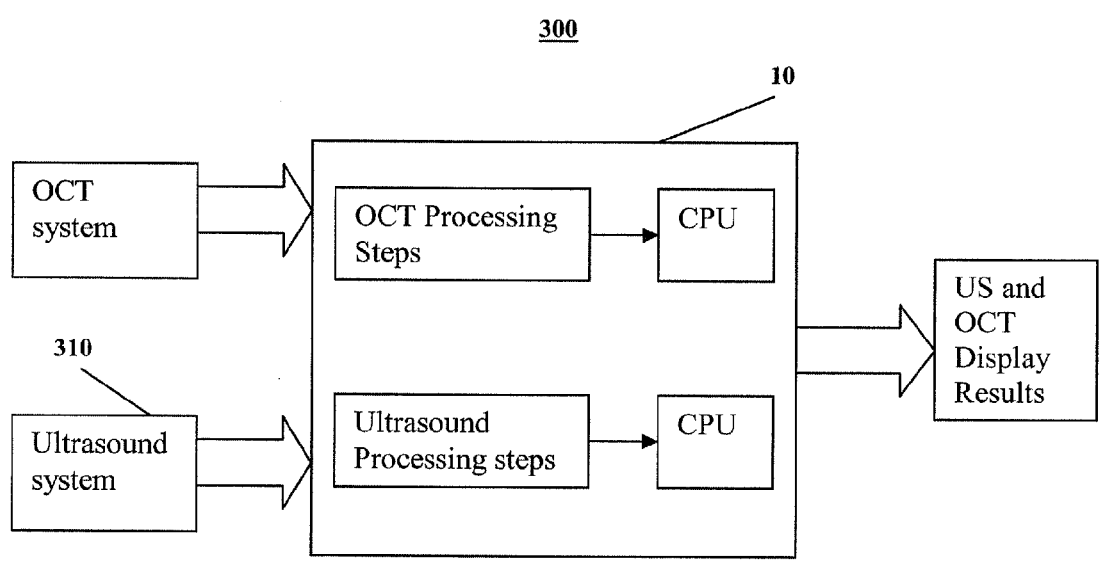
FIG. 8 is one embodiment of the invention.

In another embodiment of the invention, a combined ultrasound ("US")/OCT system 300 leverages the distributed computing system 10 platforms for real time optical and ultrasound imaging, as shown in FIG. 8. The US system 310 and the OCT system could share computers on the network for common tasks, as well as have separate computers for differing tasks linked in with common computers. In one embodiment of the invention, the OCT and US systems could have separate acquisition and processing computers, but a common display computer. The computer clusters do not necessarily have to be packaged in individual cases, as they can all appear to be a single computer from the outside. US systems include pre-processing and post-processing steps that benefit from the distributed computing system 10.

The US imaging systems can be equipped with a 38 mm aperture, broadband (5-10 MHz) linear array transducer. Cells can be imaged in color power Doppler, power Doppler, M-mode and B-scan modes. B-scan sonogram images, also called the grayscale mode, are the typical ultrasound method to monitor or examine the human body using backscattering of acoustic waves. M-mode ultrasound employs a sequence of scans at a fixed ultrasound beam over a given time period. M-mode is used for visualizing rapidly moving subjects, such as heart valves. Compared to conventional B-scan images, Doppler ultrasound is used to assess changes in the frequency of reflected acoustic waves. Color power Doppler converts reflected acoustic waves that are Doppler shifted into colors that overlay the conventional B-scan images and can indicate the speed and direction of moving objects. Power Doppler ultrasound is most commonly used to evaluate moving objects and has higher sensitivity than the color power Doppler mode. The gain of the color power and Doppler imaging mode can be manually adjusted to suppress the background noise. If the settings of the ultrasound instrumentation remain unchanged, objective comparisons of each can be made.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

The invention claimed is:

1. A method for computing optical image data comprising the steps of:
   providing at least one graphics processing unit in communication, through a communication link, with at least one central processing unit for processing optical and ultrasound image data from a combined ultrasound (US)/optical coherence tomography (OCT) system, wherein the optical image data is generated by a swept-source OCT instrument;
   using the at least one graphics processing unit to perform a Fourier Transformation processing step on the optical image data;
   using the at least one central processing unit to perform a data acquisition step, a pre-processing step, and any other processing steps on the optical image data, wherein data acquisition step comprises synchronizing the swept-source optical coherence tomography instrument by clocking a light source, wherein one of the at least one central processing units performs at least one task on the optical image data and at least one task on the ultrasound image data; and
   transmitting the processed optical image data and ultrasound image data to a display device to thereby display images at real-time frame rates.

2. The method of claim 1, wherein the any other processing steps comprise the steps of post-processing, image display, and post-display interaction.

3. The method of claim 1, wherein data acquisition comprises triggering instrumentation and digitization of the optical imaging signal.

4. The method of claim 1, wherein pre-processing comprises noise removal, windowing and apodization, and interpolation to linear wavenumber space.

5. The method of claim 2, wherein post-processing further comprises at least one of filtering, edge detection, feature extraction, and mapping polar representations.

6. The method of claim 2, wherein post-display interaction comprises at least one of requesting additional post-processing, interactive processing, measurement of image features, and playback control.

7. The method of claim 1, further comprising using the at least one graphics processing unit and the at least one central processing unit for performing ultrasound imaging.

8. A processing system for computing image data comprising:
   a combined ultrasound (US) and swept-source optical coherence tomography (OCT) system configured to generate ultrasound image data and optical image data;
   a graphics processing unit configured to perform a Fourier Transformation processing step on the optical image data; and
   a central processing unit configured to perform data acquisition, pre-processing, and all other processing steps on the optical image data, wherein data acquisition comprises synchronizing the swept-source optical coherence tomography instrument by clocking a light source, wherein the central processing unit performs at least one task for both the ultrasound image data and the optical image data;
   a display for displaying the processed optical image data; and
   a communication link providing data communication between the graphics processing unit, the central processing unit, and the display.

9. The processing system of claim 8, further comprising at least a memory for data storage.

10. The processing system of claim 9, further comprising a user interface.

11. The processing system of claim 8, further comprising an ultrasound system in communication with the graphics processing unit and the central processing unit.

12. The processing system of claim 10, wherein the user interface is in communication with the graphics processing unit and the central processing unit.

13. A processing system for computing image data comprising:
   a combined ultrasound (US) and optical coherence tomography (OCT) system configured to generate ultrasound image data and optical image data and in communication with a central processing unit and a graphics processing unit;

wherein the graphics processing unit is configured to perform a Fourier Transformation processing step on the optical image data; and wherein the central processing unit is configured to perform data acquisition, pre-processing, and all other processing steps on the optical image data and at least one task on the ultrasound image data.

14. The processing system of claim 13, further comprising a user interface.

15. The processing system of claim 13, further comprising an ultrasound system in communication with the graphics processing unit and the central processing unit.

16. The processing system of claim 14, wherein the user interface is in communication with the graphics processing unit and the central processing unit.

* * * * *